United States Patent [19]

Ziegelhoffer et al.

[11] Patent Number: 5,421,924
[45] Date of Patent: Jun. 6, 1995

[54] APPARATUS AND METHOD FOR ULTRASONIC SEALING DISPOSABLE DIAPERS

[75] Inventors: Paul Ziegelhoffer, Greenleaf; Gary E. Johnson, Green Bay, both of Wis.

[73] Assignee: Paper Converting Machine Company, Green Bay, Wis.

[21] Appl. No.: 161,782

[22] Filed: Dec. 2, 1993

[51] Int. Cl.6 .................. B32B 31/20; B29C 65/08
[52] U.S. Cl. .................. 156/73.1; 156/290; 156/308.4; 156/553; 156/580.1
[58] Field of Search .............. 156/73.1, 290, 324, 156/308.4, 553, 580.1, 580.2, 164, 504, 515; 264/23; 425/174.2

[56] References Cited

U.S. PATENT DOCUMENTS

| | | |
|---|---|---|
| 3,733,238 | 5/1973 | Long et al. ............ 156/580.1 X |
| 4,227,959 | 10/1980 | Brown ..................... 156/515 |
| 4,414,045 | 11/1983 | Wang et al. ............ 156/580.1 X |
| 4,713,132 | 12/1987 | Abel et al. ............ 156/73.1 |
| 4,862,673 | 9/1989 | Francioni ............ 156/515 X |
| 4,949,846 | 8/1990 | Lakey .................. 156/515 X |

*Primary Examiner*—David A. Simmons
*Assistant Examiner*—J. Sells
*Attorney, Agent, or Firm*—Tilton, Fallon, Lungmus & Chestnut

[57] ABSTRACT

A method and apparatus for transversely sealing multiply diaper webs including an ultrasonic horn assembly above the web and an anvil assembly below the web, and including orbiting the two assemblies with points of orbit intersection at two spaced apart points on the web and with one of the assemblies being resiliently mounted so as to yield when the two assemblies come in contact during sealing.

14 Claims, 8 Drawing Sheets

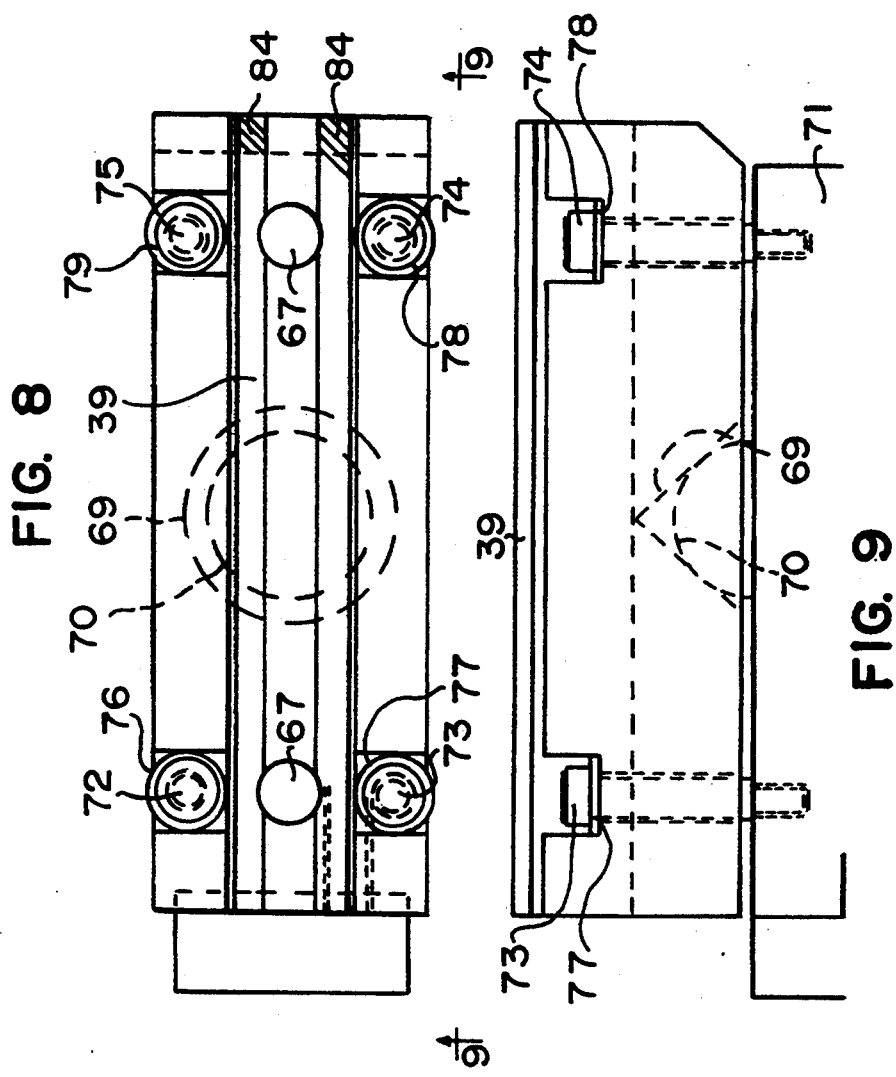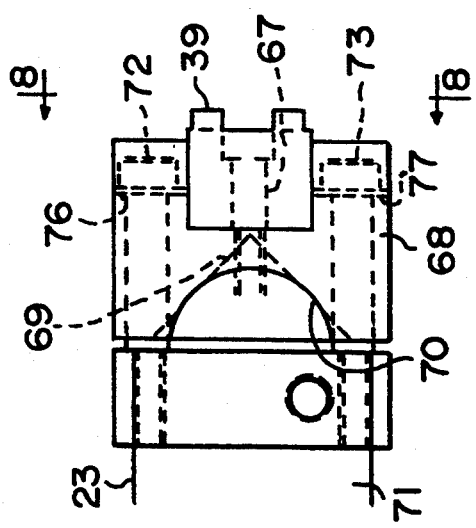

APPARATUS AND METHOD FOR ULTRASONIC SEALING DISPOSABLE DIAPERS

BACKGROUND AND SUMMARY OF INVENTION

This invention relates to apparatus and method for ultrasonic sealing disposable diapers and, more particularly, to sealing with an orbitally movable horn and anvil.

It is known that ultrasonic sealing is commonly used in many applications to weld various types of web materials together. A majority of these applications utilize a stationary mounted ultrasonic member (power supply, converter, booster, horn) in connection with a rotating patterned anvil roll member. The horn is the part of the vibratory or ultrasonic member that comes in contact with the product and effects sealing in combination with the anvil. The vibratory energy is transferred directly to the webs as they pass through these members causing them to melt and bond to each other. This approach, because of its tangential contact time, is limited to speeds and construction that require a minimal seal time.

One current apparatus employs a shuttle mechanism to increase sealing time. The vibratory member clamps down on the web with an anvil member underneath and travels with the web for a predetermined distance where it releases—having sealed a specific area—and returns to the starting point for another cycle. This is a chain drive system with complicated dynamics which makes it difficult to control.

Ultrasonic sealing on the fly has been successful because of the small area that the vibratory member has been required to seal, i.e., tangential contact to the patterned anvil roller. The drawbacks to this system are limited web speed, the product orientation required for a good seal and is limited to putting a good seal only on small areas.

The problem is that many product constructions, such as training pants, require a substantial increase in seal time due to the multiple webs and the increased sealing area. To run these on present systems would require a slower web feed rate making it more costly and changing the orientation of the web or product as it passes.

SUMMARY OF INVENTION

The invention solves the above shortcomings by applying orbital motion to the ultrasonic member along with adjusting the centerline distance between them. This varies the distance traveled while the horn and anvil are in contact.

This adjustment allows the two members to contact the web at various angular positions and travel with the web, resulting in an increase in sealing time. The orbital motion is achieved by mounting an ultrasonic member on a mounting plate and attaching the plate to two orbital support arms so that the mounting plate maintains the same orientation (i.e., vertical) as it rotates. On the other end the orbital support arms are counterweighted to balance the vibratory member while it is rotating. The ultrasonic member is fixed in its mounting bracket and cannot move, hence it makes a complete 360° circular orbit while remaining in the same vertical orientation.

Opposite the ultrasonic member is the patterned anvil member. The anvil itself is the part of the sealer that contacts the opposite side of the product that the horn seals against and the pattern on the anvil will be the pattern of the seal on the product. Located just below the anvil is an airmount actuator designed to collapse while the horn of the vibratory member and the anvil are in contact. The airmount actuator is also used to determine the amount of anvil-horn pressure during sealing. The anvil and airmount actuator are mounted on a plate (similar to the ultrasonic member) and which is mounted on two orbital support arms with counterweights. Thus, it maintains its orientation in the same manner as the ultrasonic member.

A cam is installed on the frame of the machine to dynamically control the path of the anvil just prior to impact with the horn to minimize the initial shock of the horn-anvil impact. The cam can also be utilized to dimensionally control the seal gap during the extended sealing cycle. A cam follower is located just below the anvil on the anvil member. This causes the anvil to deviate from its circular path just prior to contact with the horn. Therefore, the amount of sealing time is a function of the circular arc of the vibratory member.

Other objects and advantages of the invention may be seen in the ensuing specification.

BRIEF DESCRIPTION OF DRAWING

The invention is described in conjunction with an illustrative embodiment in the accompanying drawing in which

FIG. 7 is a side elevational view of the anvil portion of FIG. 6 and as viewed along the sight line 7—7 applied to FIG. 6;

FIG. 8 is a top plan view of the anvil of FIG. 7 as seen along the sight line 8—8 applied to FIG. 7;

FIG. 9 is an end elevational view (considered in the machine sense as looking from the discharge end) of the anvil of FIGS. 7 and 8;

DETAILED DESCRIPTION

Figure 1:
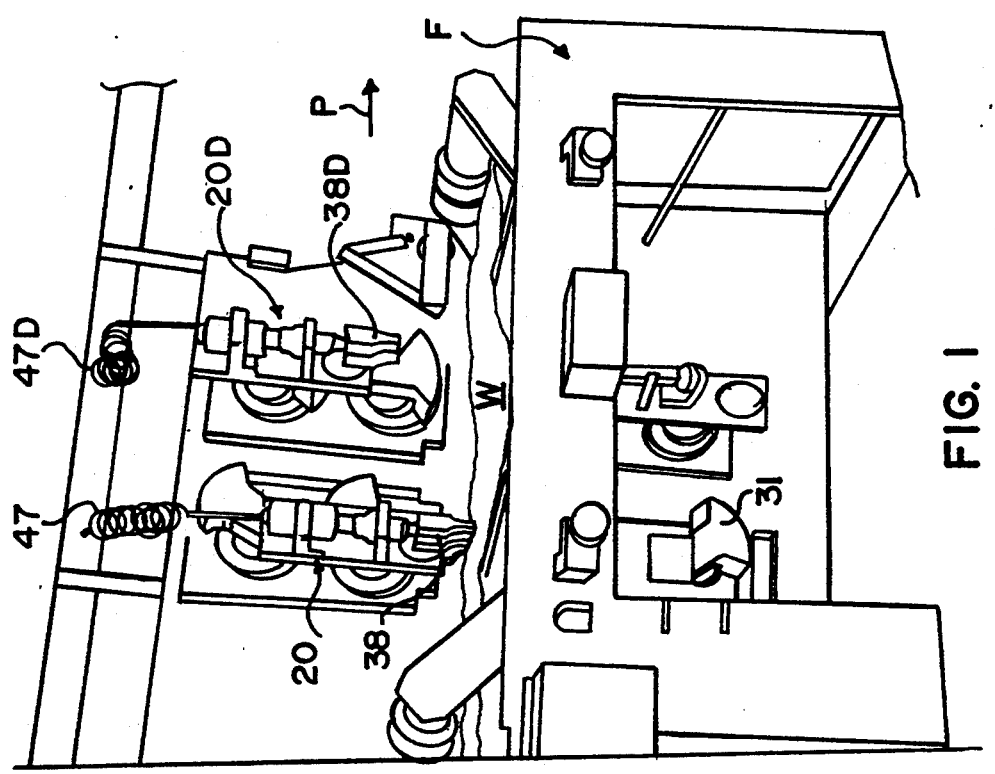
FIG. 1 is a fragmentary perspective view of a diaper machine featuring the sealing assemblies of the instant invention.

In the illustration given and with reference first to FIG. 1, the symbol F designates generally the frame of the diaper machine. The symbol W at the center of the view designates the multi-ply web which is traveling to the right along path P and which will be transversely sealed by the sealing assembly or assemblies of the invention. For example, two such sealing assemblies generally designated 20 and 20D are shown. A lesser or greater number many be employed. The assemblies are identical—and the D designating that the right hand assembly is "downstream".

Figure 6:
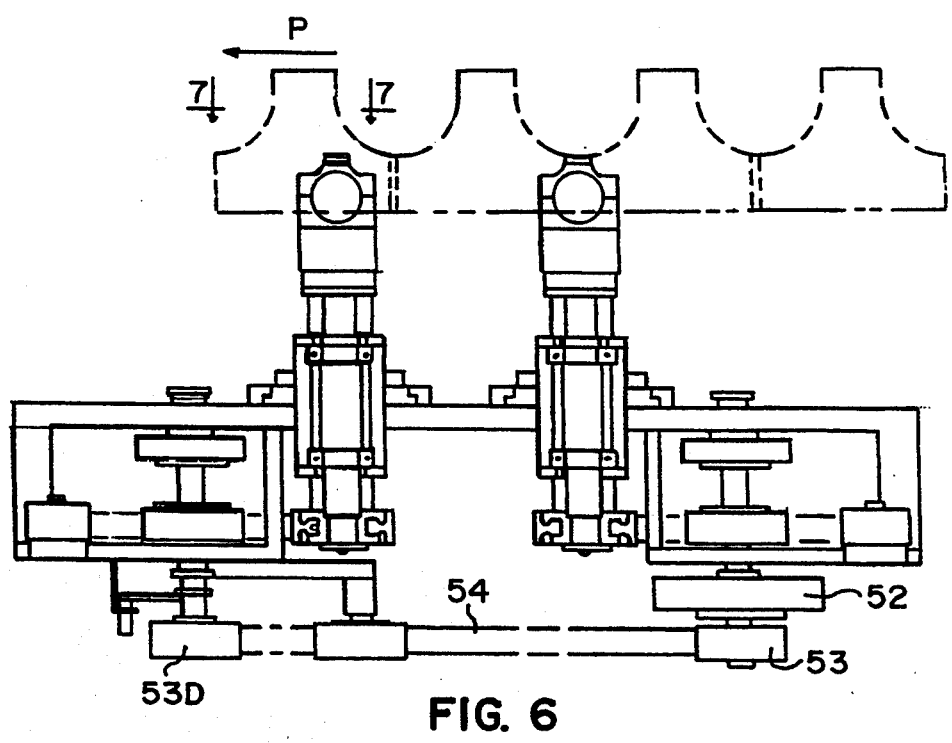
FIG. 6 is a top plan view of the drive elements of FIGS. 4 and 5.

Normally, the diaper web W may include a layer of polyethylene constituting a moisture impervious barrier, a layer of non-woven which is moisture pervious and positioned adjacent the wearer's body and a layer of absorbent fluff sandwiched between the polyethylene and non-woven layers. More layers may be employed but, in any event, it is necessary to seal between adjacent diaper configurations—see the seals S in FIG. 6.

Figure 2:
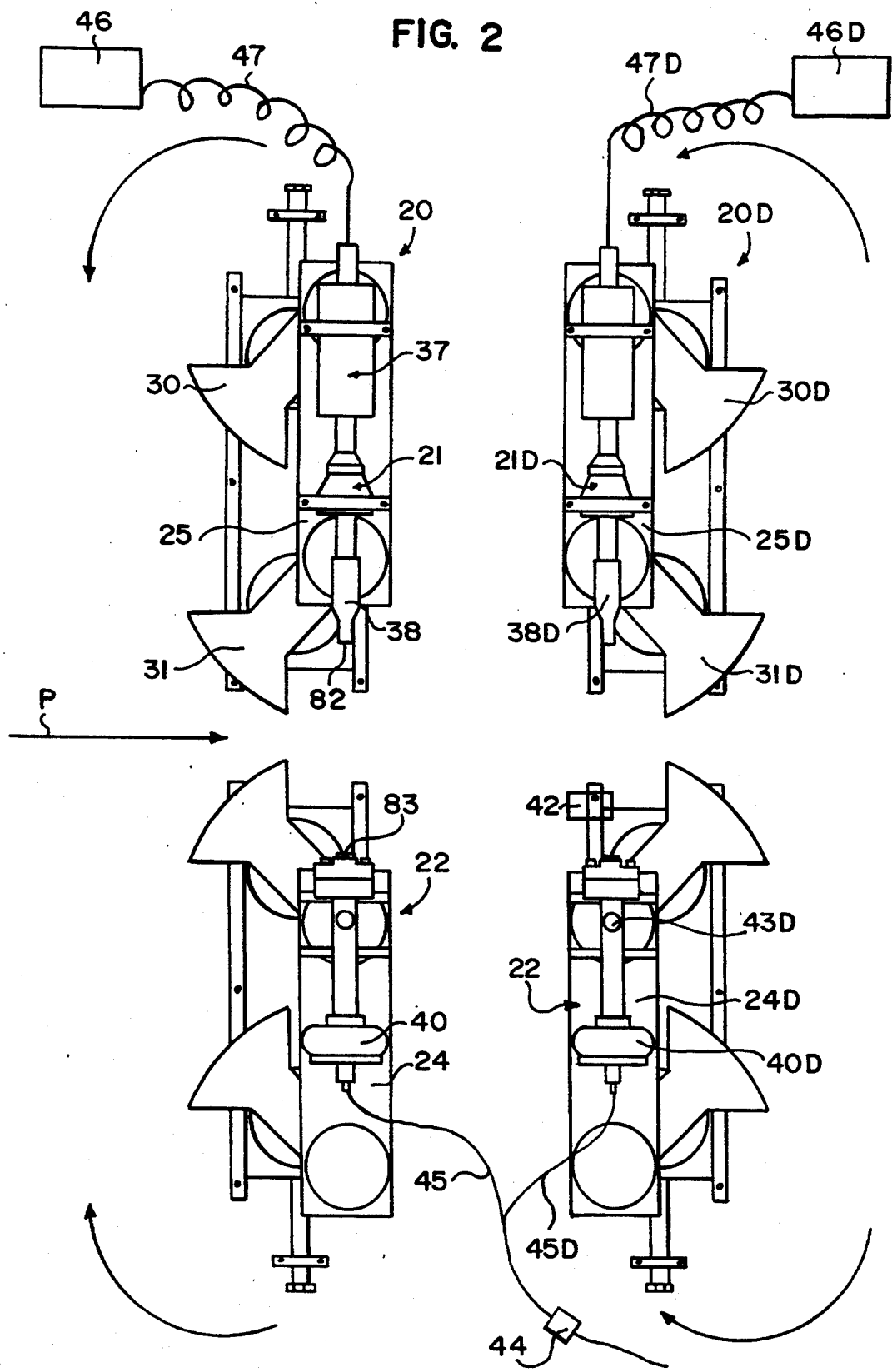
FIG. 2 is a schematic representation of the two sealing assemblies seen in FIG. 1 and corresponds essentially to a side elevational view.

Referring to FIG. 2, it will be noted that each of the assemblies 20, 20D includes an upper ultrasonic or horn assembly generally designated 21 and a lower anvil assembly generally designated 22. The sealing assemblies 20, 20D are identical (except for placement along the length of the machine) so what is described relative to one, applies to the other. The horn assemblies 21 as seen in the upper portions of FIG. 2 while the anvil assemblies 22 is seen in the lower portions of FIG. 2.

Figure 11:
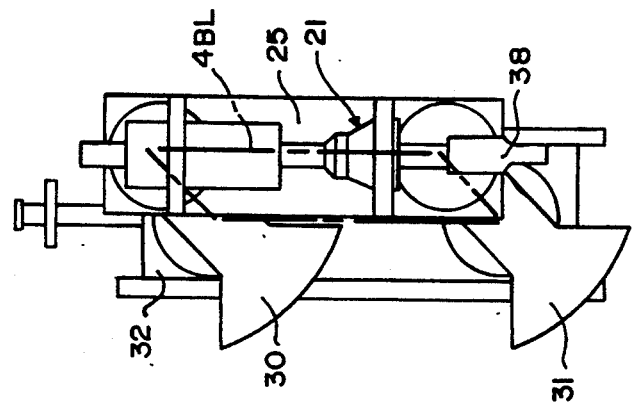
FIG. 11 is a schematic side elevational view of the vibratory assembly of FIG. 10.
Figure 10:
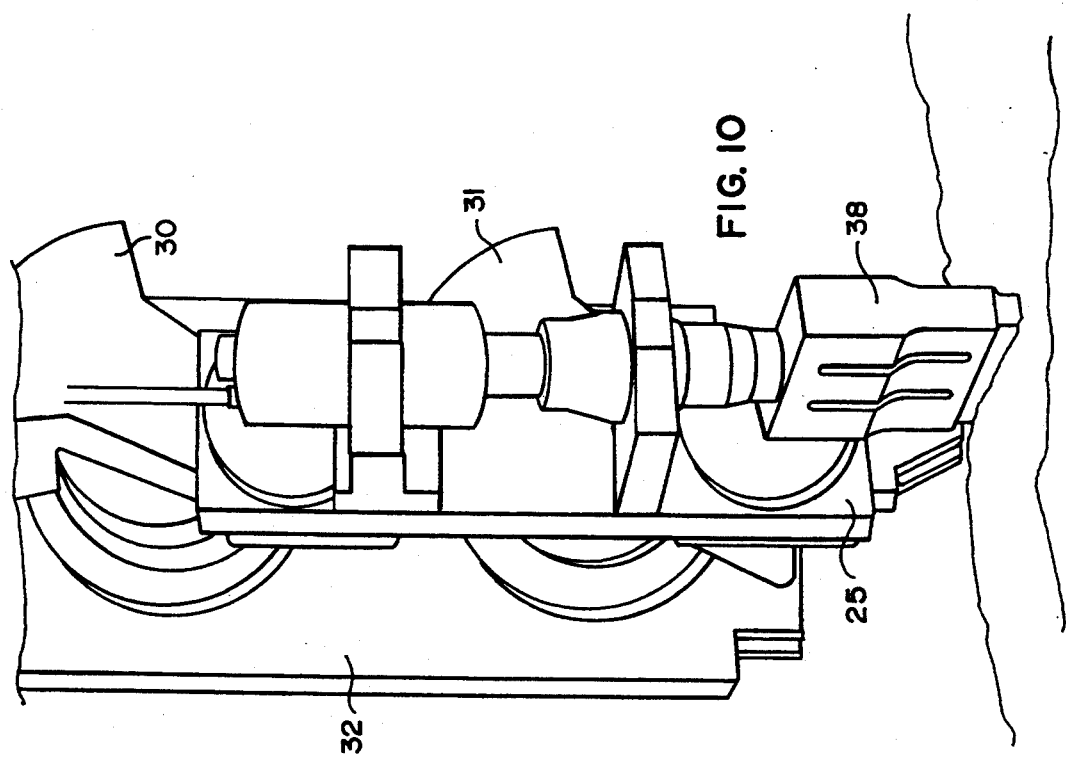
FIG. 10 is a perspective view of the vibratory assembly portion of FIG. 1.

Because of a four-bar linkage mounting, the assemblies 21 and 22 maintain their same orientation throughout the orbit, i.e., vertical as illustrated in FIG. 2. The four-bar linkage construction is schematically represented in FIG. 11 relative to the assembly 21. Each assembly not only includes the horn or anvil itself but also the associated four-bar linkage.

Figure 13:
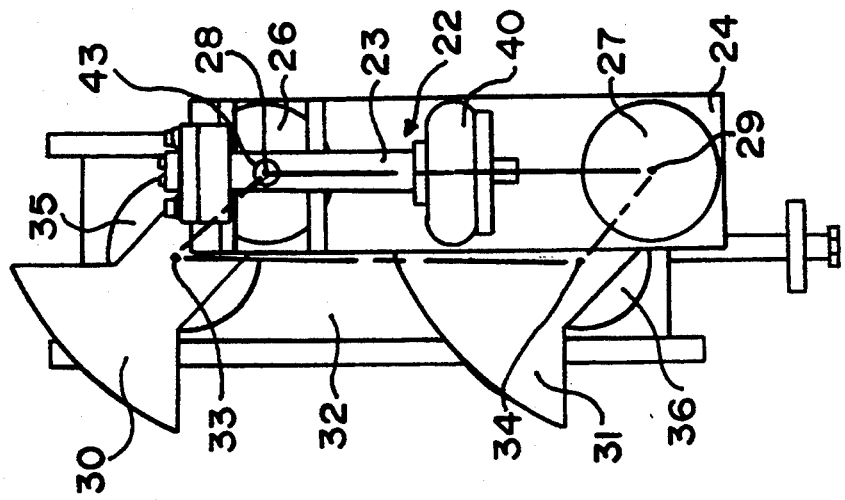
FIG. 13 is a schematic side elevational view of the anvil assembly of FIG. 1.
Figure 12:
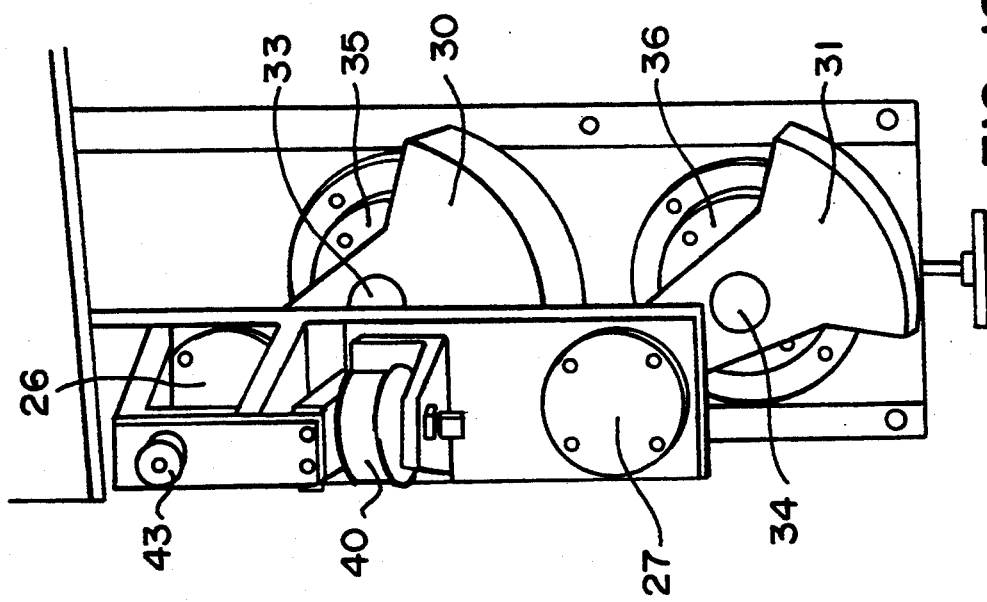
FIG. 12 is a perspective view of the anvil assembly portion of FIG. 1.

Thus, as seen in FIG. 13, the anvil assembly 22 includes a sub-assembly 23 which is positionably fixed to a movable mounting plate 24. The upper assembly 21, i.e., the horn assembly has a slightly different plate 25 which will be described hereafter.

Figure 5:
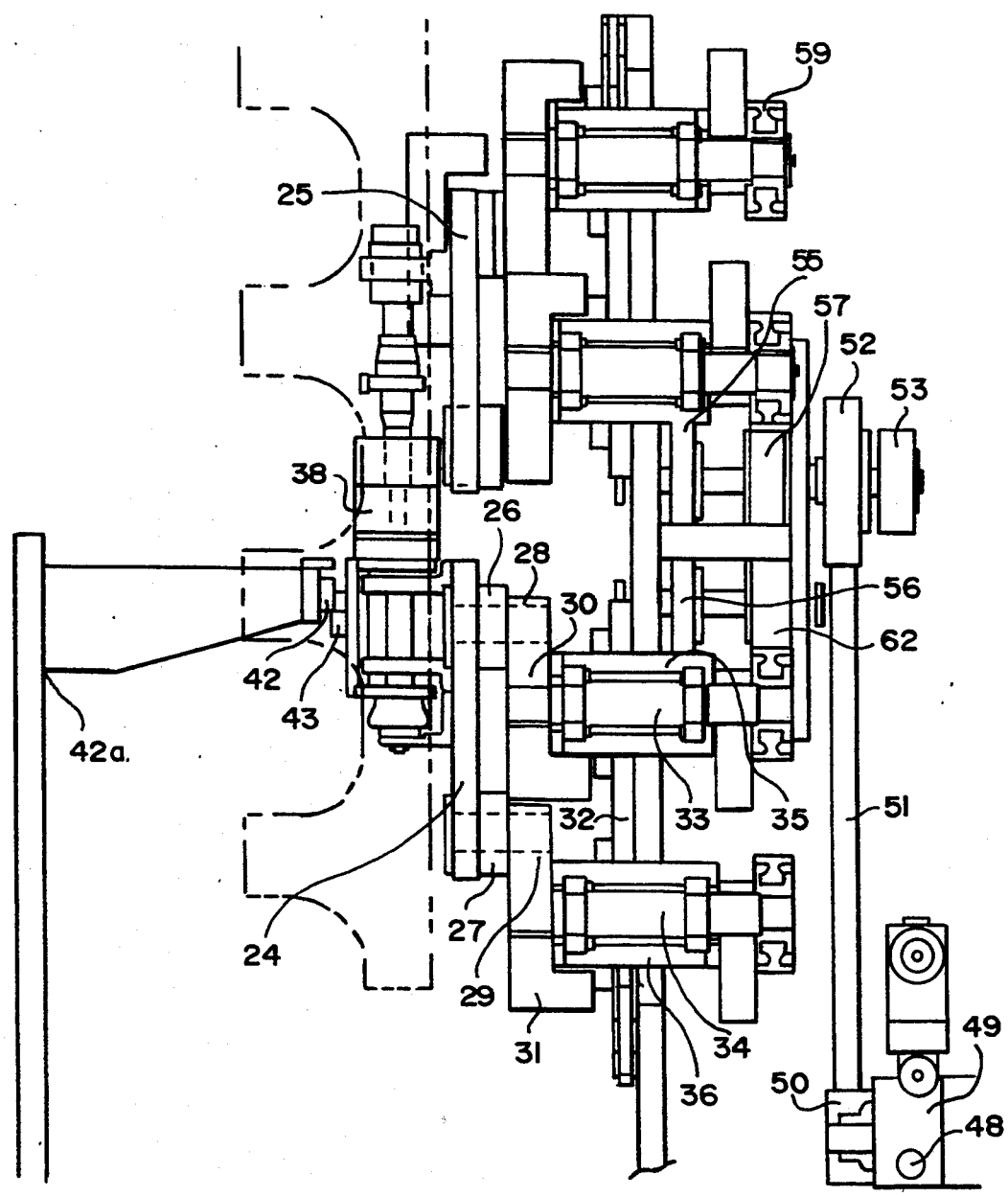
FIG. 5 is an end elevational view showing the drive elements of FIG. 4 and as seen along the sight line 5—5 of FIG. 4.

The lower assembly plate 24 is equipped with upper and lower bearings 26, 27 which receive shafts as at 28, 29 from counterweight arms 30, 31—see also FIG. 5. Each arm 30, 31 is equipped with a shaft for rotatable mounting within a bushing carried by a stationary plate 32. More particularly, the arms 30, 31 are equipped with shafts 33 and 34 (see FIG. 5 again) which are journaled in bushings 35 and 36 respectively—carried by the stationary plate 32. Thus, the four-bar linkage 4BL—as seen in FIG. 11 includes as vertical members, plates 25 and 32 and as rotatable members, the counterweight arms 30 and 31.

The various components just listed will be described in greater detail in conjunction with FIG. 5 which is also used to illustrate the drive for orbiting the anvil sub-assembly 24 and the horn sub-assembly 37.

As the sub-assemblies 23, 37 orbit, the horn itself (designated 38) comes into contact with the anvil 39— see the upper and lower left hand portions of FIG. 2. It is intended that the orbits of the two assemblies 24, 37 overlap as in seen in FIG. 3. The upper orbit which is designated 37a is that described by the horn sub-assembly 37 while the lower orbit which is designated 23a is the path traced by the anvil sub-assembly 37. To permit the orbit of one of the assemblies (or both) to depart from being exactly circular, we provide a resilient means in the form of an air-mount cylinder 40 on the anvil assembly 22 (see the lower left hand portion of FIG. 2). This permits the anvil to be forced downwardly to provide an essentially flattened portion of the orbit 23a as at 41 in FIG. 3.

Also assisting in the depression of the anvil assembly 22 is a fixed cam 42 (see the lower right hand portion of FIG. 2). This cam is supported in a stationary fashion on the frame via an arm and post arrangement generally designated 42a and which is seen in the left central portion of FIG. 5.

As the anvil assembly 23 orbits, a cam follower 43 (see FIG. 5 and the lower right hand portion of FIG. 2 at 43D) comes in contact with the cam 42 to force the anvil assembly 22 downwardly so as to provide the flattened orbit portion 41. The invention also contemplates both of the horn and anvil assemblies compressing and creating a straight line for the horn/anvil contact time.

The radius of rotation of the horn 38 is chosen to be smaller than the radius of the anvil rotation to better match anvil to horn speed and to give the anvil more time to alter its course via the cam 42 before impact with the horn. For a 13¾" long product the radius of the horn rotation is 4⅜" and the radius of the anvil rotation if 4-7/16". This gives the sealer about 30 milli-seconds of seal time at 350 diapers per minute at about 26° radial contact. The orbital support arms are adjustable to vary the size of the orbits of the horn and anvil to accommodate various sized products. The sealer is set up to accept the product (i.e., diapers) on a flat horizontal surface. The path of the product deviates only by the amount of the horn/anvil contact arc but the large amount of flex in the material makes the distance negligible. The horizontal speed of the product is matched to the tangential speed of the horn. The invention also works with the horn and anvil assemblies 22, 23 having the identical radii of rotation.

When using ultrasonic sealing, four variables exist that can be manipulated to create a good seal:

(1) Time—the amount of horn/anvil contact time to create a seal;

(2) Pressure—the amount of horn/anvil pressure required to create seal;

(3) Amplitude—this controls the height of the vibration which speeds up the rise in sealing temperature; and (4) Size of the sealing area—if all other variables are maximized, the size of the sealing area can be maximized.

The average amount of sealing time required to dynamically seal the product is 0.030 ms and the time can be adjusted to range between 0.000 ms and 0.060 ms. Dynamic sealing requires more time than static sealing. The average length of the product is about 14", the sealer can range from 12" to 16". Product feed speed average is about 350 dpm with a machine range from 0–400 dpm. With two sealing units the rpm per unit is 175. However, if 3 or more units are used, the rpm would be reduced but radius of rotation would increase accordingly. The amount of seal pressure is controlled by the airmount actuator 39. At 60 psi the actuator delivers approximately 300 lbs sealing pressure, however this can vary from 20 psi to 90 psi.

Again referring to FIG. 2 at the lower right, the numeral 44 denotes a source of pressure fluid (preferably air) which is connected by lines 45 and 45D to the airmount actuators or resilient means 40, 40D.

In similar fashion, sources of ultrasonic energy are provided as at 46 and 46D at the upper parts of FIG. 2 and which are operably connected by wires 47, 47D to the horns 38, see also FIG. 1.

We now turn to the means for orbiting the horn and anvil assemblies 21, 22 and in general this is provided by four shafts with pulleys attached for each horn/anvil sealing assembly. These are extended through the frame or plate supporting the horn or anvil. For example, in the case of the anvil 39, the mounting plate is designated 24 and for the horn assembly 37 the plate is designated 25 (see the left hand upper portion of FIG. 2). These allow the sealing assemblies to be timed and driven from the back of the unit as will be brought out subsequently relative to FIGS. 4–6. The counterweights, previously mentioned in conjunction with arms 30, 31, are paired with counterweights on the rear of the machine if necessary. In some instances, the amount of space on the front of the machine, i.e., that seen in FIG. 1 did not allow for the total amount of counterweight installed so it was added on the back of the machine. Openings are cut in the framework behind each assembly to allow shafts to pass through, the opening also enabling the assemblies to be slid up or down to increase or decrease seal time as needed—or as needed for increased or decreased arm length which could change the diaper "repeat", i.e., length. Inasmuch as the four-bar linkage for the horn assembly 21 is the same as for the anvil assembly 22, the same numerals are employed in most instances, viz., arms 30, 31, and stationary plate 32, but not plates 24, 25. These differ because of the sealing elements they carry and also because of the pin and yoke alignment means to be described hereinafter.

Orbital Drive

Figure 4:
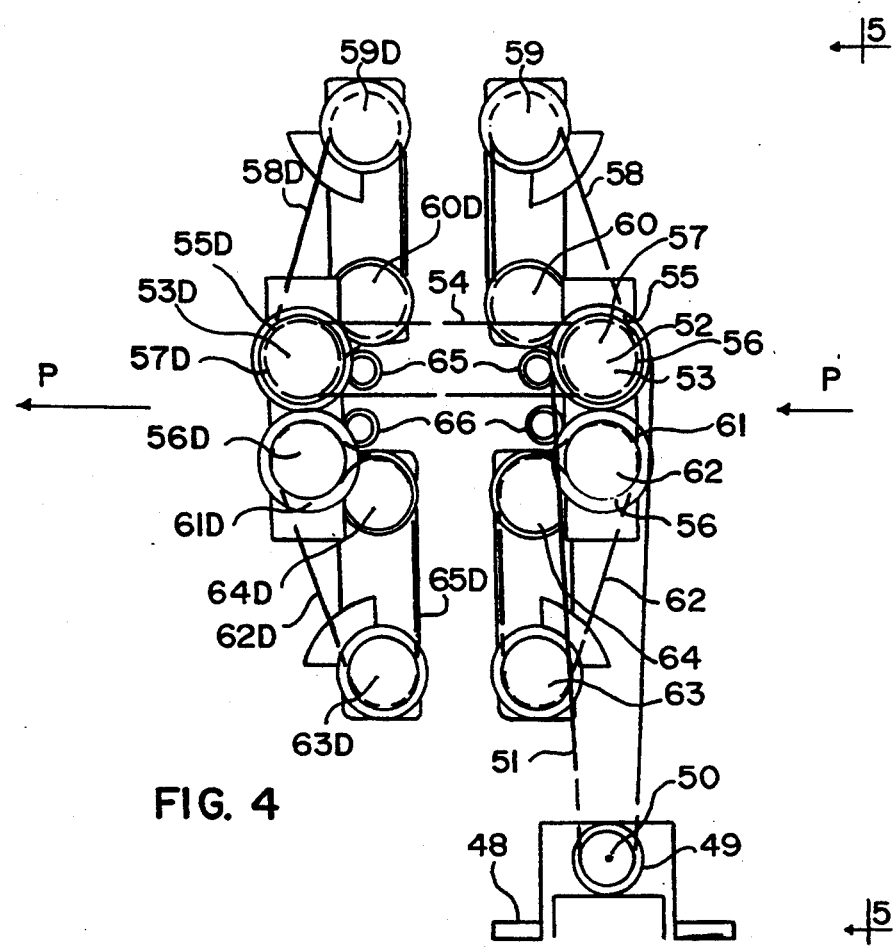
FIG. 4 is another schematic side elevational view of the portion of the machine of FIG. 1 that carries the sealing assemblies—this view being from the "drive" side, i.e., opposite to that of FIG. 1 which could be considered to be the "operator's" side, and which shows the belt-pulley and gear means for driving the orbital assemblies.

Referring first to FIGS. 4 and 5, the numeral 48 designates a lineshaft which drives the other repeating components in the line. Timing belts with appropriate pulleys are employed as can be appreciated from the right hand portion of FIG. 5. The lineshaft 48 is equipped with a gearbox 49 carrying toothed pulley 50 which entrains a tooth belt 51 and which in turn delivers rotational power to an upper pulley 52. The same can be seen at the right hand side of FIG. 4.

As mentioned previously, FIG. 4 is seen from the drive side of the machine as can be appreciated from the direction to the left of the path arrow P—as contrasted to FIGS. 1 and 2 where the arrow is directed to the right.

Coaxial with the pulley 52 is pulley 53 which is connected by belt 54 to a pulley 53D of the downstream vibratory unit. Mounted co-axially with each of the pulleys 53, 53D are gears 55 and 55D respectively. These mesh with gears 56 and 56D on the anvil assemblies.

Pulleys 57 and 57D which are coaxial with pulleys 52, 53 drive the belts 58 and 58D which, in turn, orbit the horn assemblies via pulley 59, 59D, 60, 60D. In like fashion, the gears 56, 56D associated with the anvil assemblies are equipped with co-axially aligned pulleys as at 61, 61D which are employed to entrain and operate belts 62, 62D respectively which drive pulleys 63, 63D, 64, 64D (see FIG. 4). Thus, high torque drive timing belts are used to drive and time the two upper vibratory assemblies 21, 21D and the two lower anvil assemblies 22, 22D. For the vibratory assembly one belt 58 is used to connect the two orbital support arm pulleys 59, 60 and one drive pulley 57. The drive pulley is also connected to another pulley and gear. The gear is used to drive the lower anvil assembly and the other pulley is used to time-tie the two units together. The anvil assembly is driven by the gear connected to a drive pulley with a timing belt connecting the drive pulley to the two orbital support arms. The system drive is attached to one of the gear/drive pulley shafts to give power to the whole unit. To keep the system in time with so many timing belts, belt tensioners are used as at 65 and 66— see the central portion of FIG. 4. Through the use of these belt tensioners, the belts are placed under substantial tension which keeps the system in time. However, the same rotational patterns and timing can be accomplished through the use of gears.

In summary, four shafts with pulleys attached for each horn anvil sealing assembly are extended through the frame of the sealing assemblies to be timed and driven from the back of the unit. High torque drive timing belts are used to drive and time the two upper vibratory assemblies 21, 21D and the two lower anvil assemblies 22, 22D. The same rotational patterns and timing can be accomplished through the use of gears.

Anvil Self-Alignment

Reference is now made to FIGS. 7–9 which depict the self-aligning feature employed in conjunction with the anvil 39. As can be seen in FIG. 7, the anvil 39 is secured by means of bolts 67 to a block 68. The block 68 is equipped with a conical cavity as at 69 which receives a hemisphere 70 mounted on the main part 71 of the anvil assembly.

Shoulder bolts as at 72–75 are ensleeved by belleville spring washers 76–79 and are extended through the block 68 to be threadably received within the main part 71—see FIG. 7. Thus, the anvil 39 is self-aligning (on the hemisphere 70) to ensure even sealing.

Figure 16:
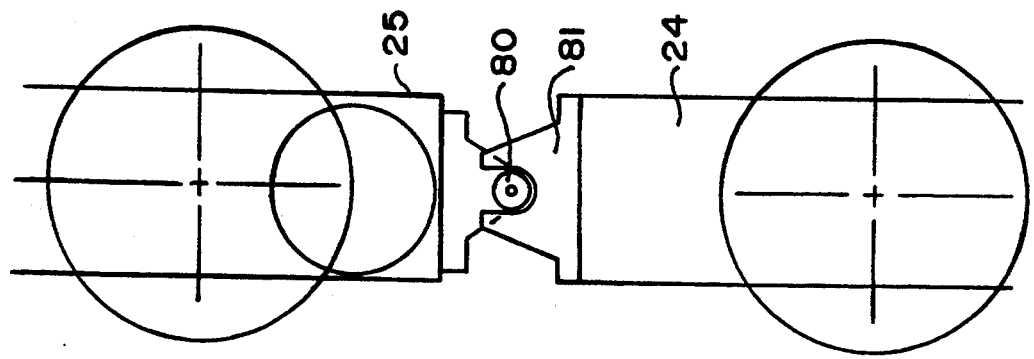
FIG. 16 is a fragmentary side elevational view similar to FIG. 2 and showing alignment means for the horn and anvil.

Further alignment means are seen in FIG. 16. There the upper plate 25 is equipped with pin means 80 which fits into a yoke 81 on the anvil plate 24.

SUMMARY OF OPERATION

The operation of the invention includes providing an elongated ultrasonic horn assembly 21 above a linear web path P and an elongated anvil assembly 22 below the path (compare FIGS. 1 and 2). Of course, the positions may be reversed but, in any event, each assembly has an end adjacent the path. As seen in FIG. 2, the horn end is 82 and the anvil end is 83. The two assemblies 21, 22 are orbited while maintaining each assembly in a vertical orientation (see particularly FIG. 2). Further, the orbit 37a for the upper assembly 22 and the orbit 21a for the lower assembly 22 intersect at two spaced apart points 41a, 41b in the path to provide the flatter orbital portion 41 (see FIG. 3). Meanwhile, a multi-ply web W is continuously advanced along the path P and the assembly ends are in resilient contact between the two spaced apart points 41a and 41b defining the segment 41 (see FIG. 3).

It may be advantageous in some instances to provide second horn and anvil assemblies along the path P but spaced a distance away from the elements 21, 22. The pair of elements 21, 22 constitute a first sealing assembly 21 (see the left hand portion of FIG. 1) while also in FIG. 1, the second pair of assemblies are designated 20D. In FIG. 2, the second assemblies are designated 21D and 22D. The distance of the second assembly 21' from the first assembly 21D is such as to position the second assembly 21D linearly away from either of the points 41a, 41b.

The segment 41 is advantageously provided by camming one of the assemblies 21, 22 away from the path P substantially at the time the assembly ends are contacted. This movement away is achieved through the use of airmount actuator or "donut" cylinder 40 (see FIG. 2). The camming is developed by virtue of providing a cam 42 on the frame F (compare FIG. 2 and the left hand portion of FIG. 5 at 43). The combination of the camming and the resilient mounting ensures the development of a suitable length of contact between the ends 82, 83 of the assemblies 21, 22. To develop an advantageous alignment of the ends of the assemblies 21, 22, i.e., the ends of the horn 38 and the anvil 39, the anvil 39 is spherically mounted as seen in FIGS. 7-9. The assembly 23 has a hemisphere 70 which is received within a conical recess 69 provided in the block 68. The block 68 in turn is resiliently secured to the lower portion of the assembly 22 by means of cap screws 72–75 each of which is equipped with a belleville spring washer 76–78.

The anvil 39 is itself removably mounted on the block 68 by means of cap screws 67 (see FIGS. 7-9). The anvil may have raised mating portions as at 84 (see the right hand end of FIG. 8) which imparts a particular pattern to the multi-ply web W. By replacing the anvil 39 with one having a differently configured pattern, that different pattern will be impressed upon the multi-ply web W.

Adjustment Features

Figure 15:
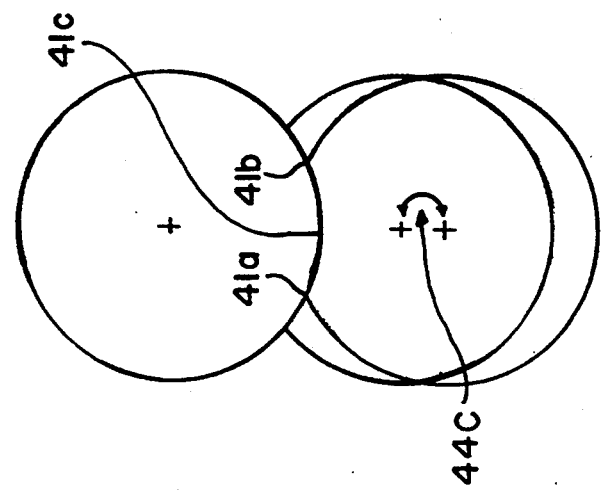
FIG. 15 is another schematic view similar to FIG. 13 and reflecting the orbit change for increased sealing time.
Figure 14:
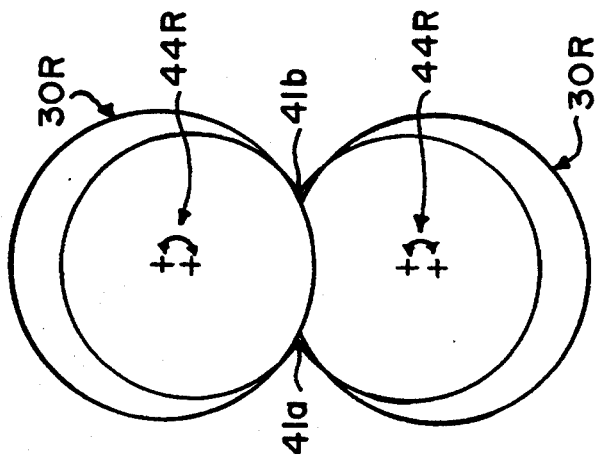
FIG. 14 is a schematic view similar to FIG. 3 bu reflecting the orbit change for increased repeat length.

These are represented schematically in FIGS. 14 and 15. In FIG. 14 by increasing the arm radius from that shown in FIG. 3, the repeat length is changed. For example, the diaper can be made longer by increasing the arm radius to 30R for both the horn and anvil. This further necessitates relocation of the centers as at 44R.

Figure 3:
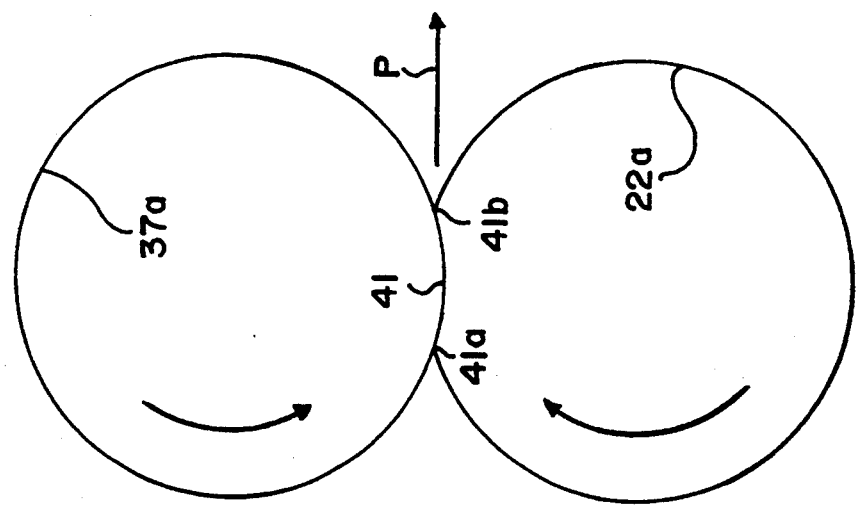
FIG. 3 is a schematic representation of the orbits of the horn and anvil parts of each sealing assembly and illustrating the period of contacting the multi-ply web.

It is also possible to change the sealing time, viz., the distance between points 41a, 41b in FIG. 3. One example is shown in FIG. 15. By moving the center 44C of the anvil orbit as shown, the points 41a, 41b are brought closer together to define a new seal spacing of 41C.

Structural Features

To provide the orbiting feature mentioned above, we employ a four-bar or parallelogram type linkage. Two of the arms are always vertical as can be appreciated from FIG. 2 which show, for example, the upper left hand assembly 21 with the counterweights 30, 31 at about 7 o'clock. When they are at 12 o'clock, the horn 38 is bottom dead center and in contact with the anvil 39. On the other hand, the counterweights 30D and 31D in the upper right hand portion of FIG. 2 are at about the 5 o'clock position and thus are proceeding toward top dead center with the horn 38 then being bottom dead center. But it will be noted that in each case the plates 24 or 24D associated with the upper and lower assemblies is vertical.

Another structural feature provided in one of the assemblies 21, 22 is the resilient means which, as illustrated, consists of an airmount cylinder or donut 40, 40D'.

We have found it advantageous to utilize airmount cylinders 40, 40D of Model No. IMIA available from Firestone Ind. Product, located at Nobelsville, Ind. The exciters 46, 46D for the horns 38, 38D are suitably Model No. 920, obtainable from Branson Ultrasonic Corp. located at Danbury, Conn.

While in the foregoing specification a detailed description of an embodiment of the invention has been set down for the purpose of illustration, many variations in the details hereingiven may be made by those skilled in the art without departing from the spirit and scope of the invention.

We claim:

1. A method of sealing a multi-ply diaper web comprising the steps of providing an elongated ultrasonic horn assembly above a linear path and an elongated anvil assembly below said path, each of said assemblies having an end adjacent said path, moving each assembly through a circular orbit while maintaining each elongated assembly in a vertical orientation and with said orbits intersecting at two spaced apart points in said path, continuously advancing a multi-ply web along said path, and resiliently contacting said assembly ends between said two spaced apart points to provide area contact between said assemblies and without relative movement between said webs and said assemblies.

2. The method of claim 1 in which said steps include providing an anvil movably mounted on said anvil assembly end and replacing a first anvil with a second anvil having a pattern for impressing on said multi-ply web different from said first anvil.

3. A method of sealing a multi-ply diaper web comprising the steps of providing an elongated ultrasonic horn assembly above a linear path and an elongated anvil assembly below said path, each of said assemblies having an end adjacent said path, orbiting each assembly while maintaining each elongated assembly in a vertical orientation and with said orbits intersecting at two spaced apart points in said path, continuously advancing a multi-ply web along said path, and resiliently contacting said assembly ends between said two spaced apart points to deform one of said orbits while clamping said web.

4. Apparatus for ultrasonic sealing of disposable diapers comprising a frame, conveyor means on said frame for advancing elongated diaper component webs along a linear path, a horn assembly including a horn orbitally mounted on said frame on one side of said path, an anvil assembly orbitally mounted on the other side of said path and aligned with said horn assembly so as to clamp said webs together for sealing the same, linkage means connecting each assembly to said frame so as to maintain each assembly in the same orientation throughout the orbit, one of said assemblies including resilient means to enable said one assembly to yield resiliently upon contact with the other of said assemblies while still clamping said webs and traveling therewith in said orientation during sealing.

5. The apparatus of claim 4 in which said anvil assembly includes a single anvil, each of said horn and anvil having an area of contact extending longitudinally of said path.

6. The apparatus of claim 4 in which said resilient means is arranged and constructed to provide a generally flat portion of the orbit of said one assembly, said flat portion being positioned adjacent said linear path.

7. The apparatus of claim 6 in which said resilient means includes airmount cylinder means.

8. Apparatus for ultrasonic sealing of disposable diapers comprising a frame, conveyor means on said frame for advancing elongated diaper component webs along a linear path, a horn assembly including a horn orbitally mounted on said frame on one side of said path, an anvil assembly orbitally mounted on the other side of said path and aligned with said horn assembly so as to clamp said webs together for sealing the same linkage means connecting each assembly to said frame so as to maintain each assembly in the same orientation throughout the orbit, one of said assemblies including resilient means to enable said one assembly to yield resiliently upon contact with the other of said assemblies, said linkage means including a four bar linkage arranged in a parallelogram for each assembly and including two plates extending perpendicular to said linear path and two arms pivotally connected at spaced apart points to each of said plates.

9. The apparatus of claim 8 in which each of said arms includes counterweight means.

10. The apparatus of claim 9 in which each counterweight means includes an enlargement at one end of each arm, said one arm end being adjacent a first plate of each linkage, said first plate being rigidly secured to said frame, a second plate of each linkage being equipped with one of aid assemblies.

11. The apparatus of claim 8 in which said apparatus includes at least two horn and anvil assemblies spaced linearly on said path to provide linearly spaced transverse seals on said web.

12. The apparatus of claim 8 in which said one of said resilient means is arranged and constructed to provide a generally flat portion of the orbit of said one assembly, said flat portion being positioned adjacent said linear path.

13. The apparatus of claim 8 in which said resilient means includes airmount cylinder means.

14. Apparatus for ultrasonic sealing of disposable diapers comprising a frame, conveyor means on said frame for advancing elongated diaper component webs along a linear path, a horn assembly including a horn mounted on said frame for movement in a circular orbit on one side of said path, an anvil assembly mounted on said frame the other side of said path for movement in a circular orbit and aligned with said horn assembly so as to clamp said webs together for sealing the same, linkage means connecting each assembly to said frame so as to maintain each assembly in the same orientation throughout the orbit, one of said assemblies including resilient means to enable said one assembly to yield resiliently upon contact with the other of said assemblies to deform the circular orbit of said one assembly during clamping of said web and to provide area contact between said horn and anvil assemblies and without relative movement between said webs and said assemblies.

* * * * *

Adverse Decision in Interference

Patent No. 5,421,924, Paul Ziegelhoffer, Gary E. Johnson, APPARATUS AND METHOD FOR ULTRASONIC SEALING DISPOSABLE DIAPERS, Interference No. 104,623, final judgment adverse to the patentees rendered November 21, 2000, as to claims 1, 3-8, and 12-14.
*(Official Gazette January 9, 2001)*